United States Patent [19]
Woodruff

[11] Patent Number: 5,328,486
[45] Date of Patent: Jul. 12, 1994

[54] SYRINGE FOR DISPENSING MULTIPLE DOSAGES

[75] Inventor: Keith F. Woodruff, Mountainside, N.J.

[73] Assignee: American Cyanamid Company, Wayne, N.J.

[21] Appl. No.: 796,046

[22] Filed: Nov. 19, 1991

[51] Int. Cl.⁵ .............................................. A61M 5/00
[52] U.S. Cl. ................................. 604/208; 604/207; 604/209; 604/220
[58] Field of Search .............................. 604/207–210, 604/218, 220, 187

[56] References Cited

U.S. PATENT DOCUMENTS

| Re. 25,113 | 1/1962 | Wilburn | 604/207 |
|---|---|---|---|
| Re. 32,974 | 7/1989 | Porat et al. | 604/208 |
| 3,563,240 | 2/1971 | Silver. | |
| 3,749,284 | 7/1973 | Kloehn | 604/208 |
| 4,153,056 | 5/1979 | Silver et al. | |
| 4,275,729 | 6/1981 | Silver et al. | |
| 4,563,178 | 1/1986 | Santeramo | 604/208 |
| 4,865,591 | 9/1989 | Sams | 604/208 |
| 4,936,833 | 6/1990 | Sams | 604/208 |
| 5,009,645 | 4/1991 | Silver et al. | |
| 5,017,190 | 5/1991 | Simon et al. | 604/208 |

FOREIGN PATENT DOCUMENTS

| 0293572 | 12/1988 | European Pat. Off. | |
| 0450905 | 10/1991 | European Pat. Off. | |
| 0882743 | 6/1943 | France | 604/207 |
| 1577954 | 8/1969 | France | 604/210 |
| 2194452 | 3/1974 | France. | |
| 0279779 | 3/1952 | Switzerland | 604/207 |
| 1212823 | 11/1970 | United Kingdom. | |
| 8101104 | 4/1981 | World Int. Prop. O. | |
| 9114467 | 10/1991 | World Int. Prop. O. | |

*Primary Examiner*—C. Fred Rosenbaum
*Assistant Examiner*—Ronald K. Stright, Jr.
*Attorney, Agent, or Firm*—Mark P. Stone

[57] ABSTRACT

A syringe for administering medicines, pharmaceuticals, and other liquid or semi-liquid materials includes a movable scale which is automatically reset to a zero position after a preselected dosage of material has been discharged from the syringe. The scale is adjustable for selecting subsequent dosages to be discharged, which may be the same or different in quantity from the previously discharged dosage. The automatic zero reset feature of the scale enables a user to administer multiple dosages of material from the same syringe, and vary the quantity of each dosage if desired, without the need to make calculations or adjust the scale to compensate for either the quantity of material previously discharged from the syringe or the quantity of material currently remaining in the syringe. The automatic zero reset function is provided by a scale which is movable, together with a slideable stop element, relative to a plunger of the syringe, and releasably lockable at preselected positions on the plunger corresponding to the quantity of material to next be discharged from the syringe. In further aspects of the invention, the front ends of the plunger and a forward container are tapered for complementary fit, and a storage element is provided on the syringe for removably retaining a cover for a discharge outlet when the syringe is being used.

15 Claims, 5 Drawing Sheets

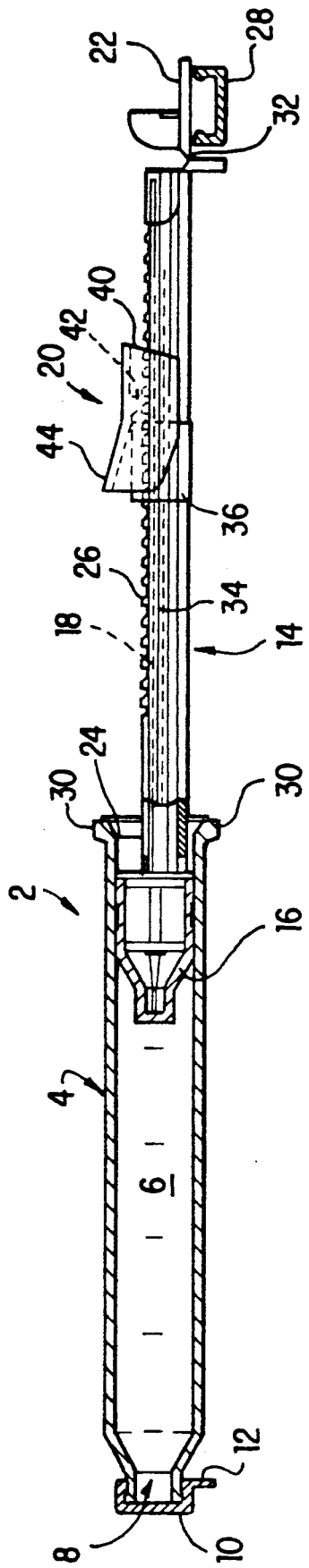
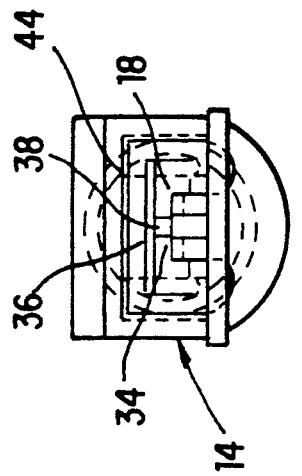
FIG. 4
FIG. 5

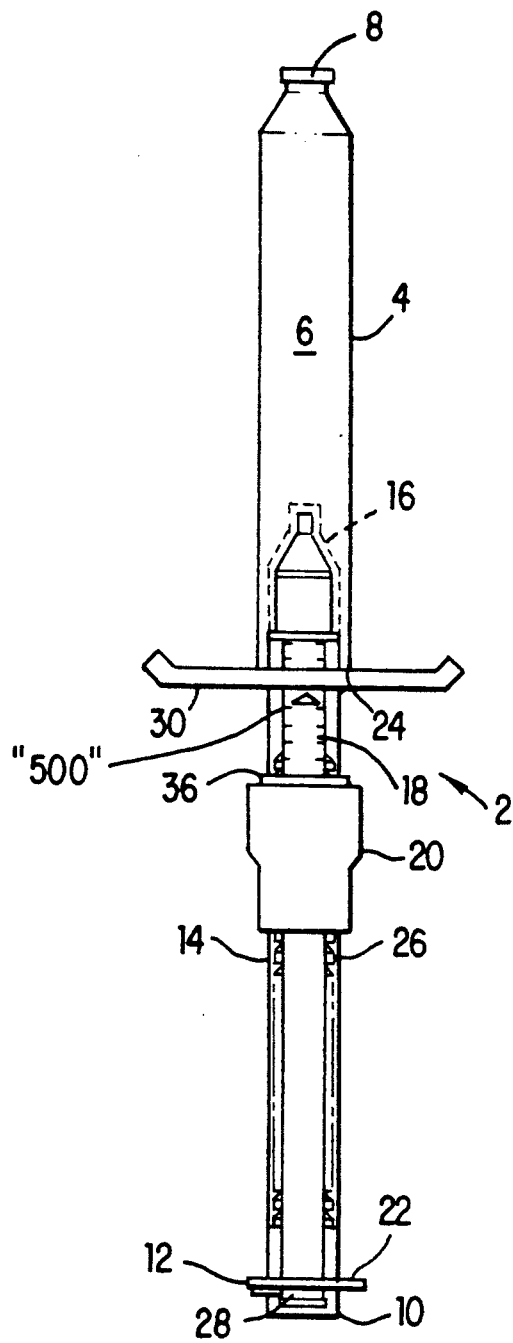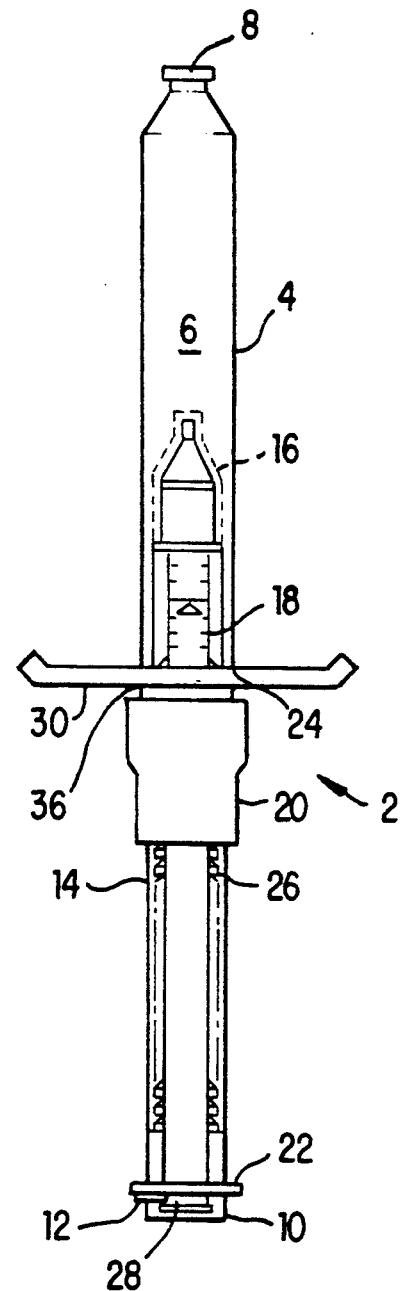
FIG. 6
FIG. 7

SYRINGE FOR DISPENSING MULTIPLE DOSAGES

BACKGROUND OF THE INVENTION

The present invention relates generally to syringes for administering liquid and semi-liquid (e.g. pastes) compositions and preparations such as medicines, pharmaceuticals and the like. The invention is more particularly directed to syringes adapted to discharge material in a plurality of separate successive, preselected dosages which may vary in quantity from each other, or which may be of the same quantity. The invention is particularly useful in connection with the administration of veterinary paste, such as that commonly administered to horses, but is not limited to this specific application.

U.S. Pat. No. 3,563,240, entitled "Dual Unit Syringe" and issued to Jules Silver on Feb. 16, 1971, is illustrative of the general state of the art. This patent discloses a syringe including a container pre-loaded with material to be administered, and a plunger received within the container for discharging separate, predetermined quantities of material from a discharge opening in the container. A scale inscribed on the plunger enables the user to select a predetermined dosage of material to be discharged from the container. The plunger includes a threaded outer surface, and a nut or other stop element is rotatable along the plunger relative to the scale on the plunger. The scale designates predetermined dosages to be administered, and the nut is moved into alignment with a desired dosage designation. The plunger is then advanced into the container until further forward movement of the plunger is prevented by the stop element abutting against the rear end of the container. Engagement of the stop against the container to restrain further forward movement of the plunger indicates that the desired preselected dosage of material has been discharged from the syringe. The scale provided on the plunger designates specific predetermined dosages, but does not indicate the specific quantity of material to be discharged from the syringe. Accordingly, any variation in the quantity of material to be discharged which differs from the preset doses designated on the scale must be based upon imprecise estimates.

PCT Patent Specification No. PCT/US80/01468 (corresponding to U.S. Pat. No. 4,275,329, issued Jun. 30, 1981) discloses a syringe (marketed under the name DIAL-A-DOSE) including a scale on a plunger designating specific quantities of material to be discharged. A stop element is formed from a ring which is slideable along the plunger to select the next desired dose to be administered by the syringe. The ring is rotatable into a locked position on the plunger after the desired dose has been set. However, after an initial dose is discharged, subsequent doses only can be set on the scale after calculations have been made based upon the quantity of material previously discharged from the syringe. For example, if the first dosage to be administered is "50" in quantity, the portion of the scale designating "50" will be aligned with the rear end of the container after the plunger has been advanced relative to the container to discharge the initial dose. The scale setting of a subsequent dosage to be administered must be based on calculations using "50" as the standard of reference. If, for example, the next dosage to be administered is "75" in quantity, the user must make a calculation to determine the total quantity that will have been discharged after the next dosage has been administered, and then retract the stop means to "125" on the scale of the plunger to assure that a quantity of "75" will next be discharged from the syringe. Continuous re-calculating, re-adjusting and re-setting the position of the stop means on the scale for each subsequent dose to be administered from the syringe is cumbersome, adversely affects the time required for administration, and is likely to result in errors in the dosages administered, particularly where numerous dosages of different quantities are to be sequentially administered.

A syringe sold under the name SLIDE-A-DOSE and marketed by Silver Research (and more fully described in U.S. Pat. No. 5,009,645, issued Apr. 23, 1991) similarly includes a scale on a plunger which requires continuous calculations based on the quantity of previously administered doses as a prerequisite to setting the next successive dose to be administered. Accordingly, the drawbacks discussed with reference to the aforementioned PCT publication, are equally applicable to this syringe. The SLIDE-A-DOSE syringe employs a stop element which is slideable along the scale of the plunger and held in a selected position thereon substantially by a knife edge carried by the stop and depressed to become embedded in a rail defined on the plunger. The knife edge is disengaged by rotatably moving the stop relative to the plunger.

It is the primary object of the present invention to provide a syringe having a scale which is automatically re-set to a zero reference position after any preselected dosage of material has been discharged from the syringe. The automatic-zero reset enables the user to set the scale for only the quantity of material to be discharged from the syringe for the next dosage to be administered, thereby eliminating the need to make calculations and adjustments to the setting on the scale to compensate for the quantity of material discharged from the syringe in prior doses. In this manner, separate, multiple dosages of material, each of which may (or may not) vary in quantity from each other, can be efficiently administered from the same syringe, thereby improving the overall efficiency of the administration procedure and eliminating the risk of administering an incorrect dosage as a result of erroneous calculations or scale settings by the user.

It is a further object of the present invention to provide a syringe for administering separate, multiple dosages of material including improved means for setting the preselected quantity of material to be administered, improved means for assembling a scale within the plunger, improved means for storing a retainer cap or closure element for the discharge outlet of the syringe when the cap is removed from the discharge outlet, and improved means for assuring that substantially the entire contents of the syringe is ultimately discharged therefrom to minimize any residue therein.

Other objects and advantages of the present invention will become apparent from the following description.

SUMMARY OF THE INVENTION

The present invention provides a syringe of the type adapted to administer separate, multiple dosages of material, each of which may be the same or different in quantity from previously administered dosages. The syringe includes a forward container portion adapted to store material to be administered by the syringe, and a plunger received within a rear opening of the container. The plunger is movable forwardly relative to the container for exerting a force on the material within the container for discharge thereof through a discharge outlet defined at the forward end of the container. The plunger includes a scale calibrated to designate the quantity of material within the container ranging between the maximum storage capacity of the container and zero contents. The scale is subdivided by gradient markings to enable precise selection of a specific quantity of material to be discharged from the syringe. The scale is movable relative to the plunger by a slide element attached to the scale at its zero indicia designation. The scale is calibrated such that when the slide element is retracted to its most rearward position on the plunger, a fixed reference position proximate to the rear end of the container (.e.g., a rear container wall) is aligned with the indicia on the scale designating the quantity of material remaining in the container.

A preselected dosage or material to be administered by the container is set by moving the slide element (and thus the scale) to a position on the plunger such that the indicia on the scale corresponding to the preselected quantity of contents to be discharged from the syringe is aligned with the fixed reference position on the container. The slide element is then releasably locked into position on the plunger, and the plunger is advanced forward relative to the container until further forward movement of the plunger is stopped by the slide element engaging against the rear end of the container. When the forward movement of the plunger is stopped, the pre-selected quantity of material has been discharged from the container. The slide element, and thus the zero setting on the scale attached thereto, is now positioned at the forwardmost portion of the plunger which still extends rearwardly from the container. The next dosage of material to be administered by the syringe is set by retracting the slide element (and thus the scale) rearwardly relative to the plunger until the scale indicia corresponding to the quantity of the next dosage is aligned with the fixed reference position on the container.

The same process is repeated for each subsequent dosage to be administered. Since the zero setting on the scale will always be positioned at the forward end of the portion of the plunger still extending rearwardly from the container after any preselected dosage has been administered, the setting of the next successive dosage is always based only upon the absolute value of the quantity of material to be next discharged, thereby eliminating the need to make any calculations or adjustments to the scale setting to compensate for the quantity of material previously discharged from the syringe.

The automatic zero reset feature of the syringe enables the same syringe to be efficiently used for administering separate, successive multiple doses of material, each of which may be of the same or different quantity than the previously administered dosage. Subsequent dosages may be quickly and precisely set on the scale based only on the specific quantity of material to be administered, thereby eliminating the need to make calculations or adjustments to the scale setting. The elimination of such calculations and adjustments significantly reduces the risk of administering incorrect dosages, a problem which occurs frequently when the same syringe is used to administer a plurality of separate dosages of varying quantities of material, and further reduces the time required to administer multiple doses to enhance the overall efficiency of the administration procedure.

The slide element of the present invention, which carries the scale and is longitudinally movable therewith along the plunger, enables the user of the syringe to readily and accurately set the quantity of material to be discharged in any dose. The slide element, which also functions as a stop, is pivotable between a first position in which it is slideable along the plunger element, and a second position in which it is selectively and releasably locked into a predetermined position on the plunger corresponding to the quantity of material to be next administered. The slide element therefore provides a stop which does not require rotational movement to adjust its position on the plunger (or to lock or unlock the slide on the plunger), and does not rely on friction fit to secure it in a desired relative position on the plunger.

The plunger includes means for providing access to the movable scale mounted therein for efficient assembly, adjustment and replacement of the scale. The plunger also includes means for removably storing a cap covering the discharge outlet of the container of the syringe when the syringe is in use and the cap is removed from the discharge outlet. A wide diameter flange mounted to the rear end of the container provides gripping means enabling a user to administer material from the syringe using only a single hand, thereby freeing the other hand to control an animal receiving material from the syringe.

The movable scale of the present invention is preferably an endless loop or tape rotatably mounted around a support element fixedly mounted within or relative to the plunger in a longitudinal orientation therewith. However, other types of movable scales can also be employed, as, for example, a retractable coiled tape having one end thereof mounted to a coil spring.

In a further aspect of the invention, the front ends of both the plunger and container of a syringe are tapered for complementary fit of the plunger within the container when the plunger is advanced into its forwardmost position within the container. In this manner, the container advantageously defines a narrow nozzle and discharge opening at the front end thereof, and the complementary fit of the plunger assures that substantially all of the contents of the container will ultimately be discharged therefrom leaving only a nominal residue.

Other advantages and benefits of the syringe in accordance with the present invention will become apparent from the following description in conjunction with the drawings described below.

BRIEF DESCRIPTION OF THE DRAWINGS

FIG. 4 of the drawing illustrates a side elevational view of the syringe illustrated by FIG. 1;

FIG. 5 of the drawing illustrates a rear elevational view of FIG. 4 in which a hinged end wall of the syringe is pivoted into an open position; and FIGS. 6–9 are top plan views of the syringe, similar to that disclosed by FIG. 1, sequentially illustrating an operating cycle of the syringe in which successive, multiple doses of different quantities are discharged therefrom.

DESCRIPTION OF THE BEST MODES FOR CARRYING OUT THE INVENTION

Figure 1:
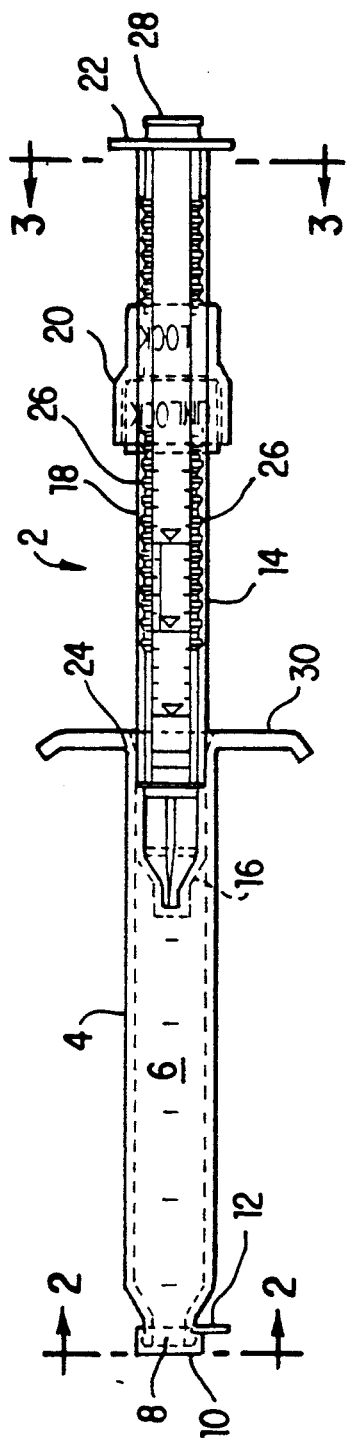
FIG. 1 of the drawing illustrates a top plan view of syringe in accordance with the present invention.
Figure 3:
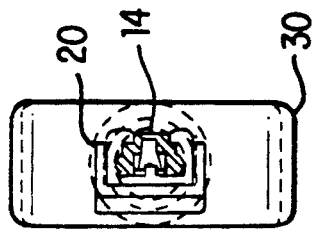
FIG. 3 of the drawing is a sectional view taken along directional arrows 3—3 of FIG. 1.
Figure 2:
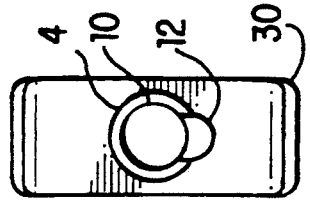
FIG. 2 of the drawing is a sectional view taken along directional arrows 2—2 of FIG. 1.

FIGS. 1–3 of the drawing illustrate a syringe in accordance with the present invention, which is generally designated by the reference numeral 2. The syringe may be of the pre-loaded disposable type, or may be of the refillable reusable type. The syring is particularly useful for administering veterinary materials, but is not limited to this particular application. The syringe includes a forward container portion 4 for storing a quantity of liquid or semi-liquid material 6 (e.g., a paste) to be discharged through a discharge outlet 8 defined at the forward end of the container portion. A cap 10 having a tab 12 is removably mounted over the discharge outlet 8 when the syringe is not in use. The forward end of the container portion defines an inward taper which terminates at the discharge outlet.

A plunger 14 is received within a rear opening of the container for slideable movement relative to the container. As the plunger is advanced forwardly within the container, it exerts a force on the material 6 therein to discharge a portion of the contents through the discharge outlet 8. The forward portion 16 of the plunger is inwardly tapered and corresponds to the configuration of the forward end of the container for providing a complementary fit therein when the plunger is moved into its forwardmost position relative to the container. The plunger carries a movable scale 18, which as will be discussed in greater detail below, enables the user of the syringe to preselect and adjust the quantity of each of the dosages of material to be administered from the forward container, without engaging in any calculations or adjustments to compensate for the quantity of material 6 previously discharged from the container. The scale 18 includes indicia corresponding to the quantity (e.g., volume) of material within the container 4, ranging from zero contents to the maximum capacity of the container when it is fully loaded.

A slide element 20 is mounted to the plunger 14 for selective longitudinal movement therealong substantially between a rear plunger wall 22 and a rear wall 24 of the container defining the rear end of the container 4. The slide element is selectively and releasably lockable at predetermined positions on the plunger by engagement of the slide element with teeth 26 defined on the upper surface of the plunger. As will be discussed in further detail below, the movable scale 18 is coupled to the slide element 20 for conjoint movement with, and relative to, the plunger to provide an automatic zero reset function after a preset quantity of material 6 has been discharged from the syringe to enable the quantity of the next successive dose to be administered to be set without making calculations or adjustments to compensate for previously administered doses. The rear end wall 22 of the plunger defines a rearwardly extending protuberance 28 adapted to removably store the container cap 10 by friction engagement thereon when the cap is removed from the forward discharge outlet 8 of the container 4. A wide flange 30 extends outwardly from substantially the rearmost portion of the container 4, and is readily gripped by a user to provide relative movement between the plunger 14 and the container 4 when the plunger is advanced into (or retracted from) the container.

FIGS. 4–5 of the drawing illustrate a side elevational view, in section, and a rear elevational view, in section, of the syringe illustrated by FIG. 1. In FIG. 4, the rear wall 22 of the plunger 14 is illustrated in its open, downwardly pivoted position, while FIG. 1 illustrates this wall in its closed position. A living hinge 32 is provided for pivoting the rear end wall of the plunger between its opened and closed positions. FIG. 4 more clearly discloses that the scale 18 is an endless loop selectively rotatable about a longitudinally extending support element 34 fixedly mounted relative to (or within) the plunger 14.

Figure 4A:
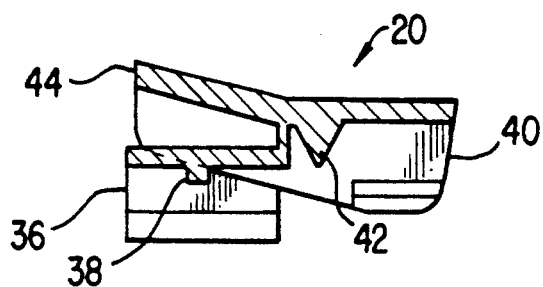
FIG. 4A illustrates a side elevational view, in section, of a slide element used in the syringe shown in FIG. 1.
Figure 4B:
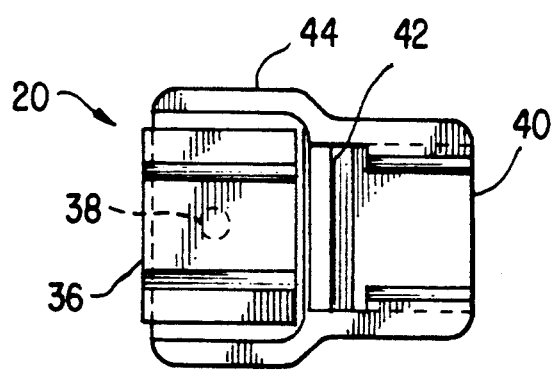
FIG. 4B illustrates a top plan view of the slide element illustrated in FIG. 4A.
Figure 4C:
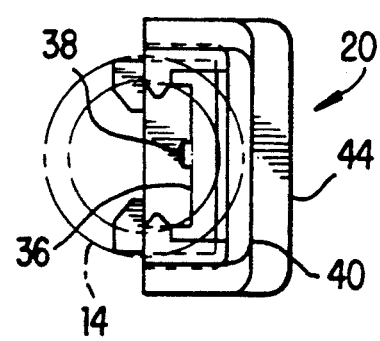
FIG. 4C illustrates a front elevational view of the slide element illustrated in FIG. 4B.

The slide element 20, shown in FIG. 4 and illustrated in greater detail in FIGS. 4A, 4B, and 4C is an elongated element comprising a forward generally "U" slide segment 36 which is retained on the plunger 14 and is slideably mounted along the upper surface of the plunger, and a rear segment 40 connected to and extending rearwardly from the forward slide segment 36 and linearly movable therewith. A lever portion 44 extends integrally from the rear segment 40 for selectively pivoting section 40 into an elevated position relative to the top surface of the plunger 14 when the lever 44 is depressed downwardly towards the top surface of forward slide segment 36. When no downward force is exerted on the lever 44, the rear segment 40 of the slide element is supported by the top surface of the plunger 14. When a downward force is exerted on the lever 44, the rear segment 40 is pivoted upwardly relative to the top surface of the plunger. The resilient force necessary to pivot the rear segment by the lever is preferably provided by forming the slide element 20 from a flexible material (such as a plastic) having a normal unstressed configuration as shown in FIG. 4A, but which may be elastically deformed to pivot segment 40 upwardly by applying a downward force on the lever 44.

Still referring to FIG. 4A, the forward slide segment 38 of the slide element 20 carries a tooth or prong 38 extending downwardly from its top surface, while the rear segment 40 of the slide element 20 carries a downwardly extending tooth 42. The tooth 42 will engage the complementary teeth 26 extending upwardly from the top surface of the plunger 14 when the rear segment 40 is in its lowermost elevated position relative to the plunger (i.e., when no downward force is exerted on the lever 44). In this position, the slide element 20 is locked at a predetermined position on the plunger, and no relative slideable movement between the slide element and the plunger is possible. By depressing the lever 44 downwardly, the rear segment 40 is pivoted upwardly relative to the top surface of the plunger, disengaging the tooth 42 from the plunger teeth 26, and thus permitting the slide element 20 to be moved selectively relative to the plunger 14. The slide element 20 eliminates the burdensome procedure of rotating a threaded element along the plunger to set the scale or to lock or unlock the slide in a selected position on the plunger, as is common to many prior art syringes, yet does not rely on friction fit, but provides positive locking engagement, to secure the slide/stop element at selected positions on the plunger.

The downwardly extending prong 38 carried by the forward slide segment 36 of the slide element 20 engages the scale 18 through a suitable opening defined therein so that the scale is movable with the slide element relative to the plunger, or the scale is releasably locked into a predetermined position relative to the plunger when the slide element is in its locked position. The scale 18 and the slideable element 20 are oriented relative to one another, as shown in FIG. 1 of the drawing, such that the zero indicia of the scale is aligned with the forward end of the forward slide segment 36 of the slide element. Longitudinal movement of the slideable element 20 relative to the plunger 14 causes the scale, which is formed as a closed, endless loop of tape, to rotate around its longitudinally extending support element 34 fixedly mounted relative to the plunger 14. The scale 18 is calibrated such that when the plunger is fully retracted from the forward container, and the slide element is in its rearmost position relative to the plunger, the forward end of the scale 18 in alignment with a fixed position proximate the rear of the forward container 4 (e.g., the rear wall 24 of the container) designates the maximum capacity of the container 4 when it is fully loaded with material 6.

FIGS. 6–9 of the drawing illustrate an operating sequence of the syringe illustrated by FIG. 1. FIG. 6 shows the rear plunger 14 substantially fully retracted from the forward container 4 which is substantially loaded with a maximum capacity of material 6. The slide element 20 is retracted relative to the rear wall 24 of the container 4. As discussed above, the scale 18 is movable with the slide element, and the zero indicia marking on the scale is aligned with the front edge of the forward segment 36 of the slide element. In the position of the slide shown in FIG. 6, indicia on the scale corresponding to a dosage of "500" is aligned with the rear wall 24 of the container. The slide element 20 is releasably locked into this position, and the plunger is advanced into the container until further forward movement is stopped by engagement of the front edge of the slide with the rear wall of the container, as shown in FIG. 7. At this position, a dose of "500" has been discharged from the container, and the zero indicia on the scale is aligned (together with the front edge of the slide 20) with the rear wall 24 of the container. The slide element is of a larger dimension than the opening in the container rear wall 24 which receives the plunger so that forward movement of the slide element relative to the container is stopped by the container rear wall.

Figure 8:
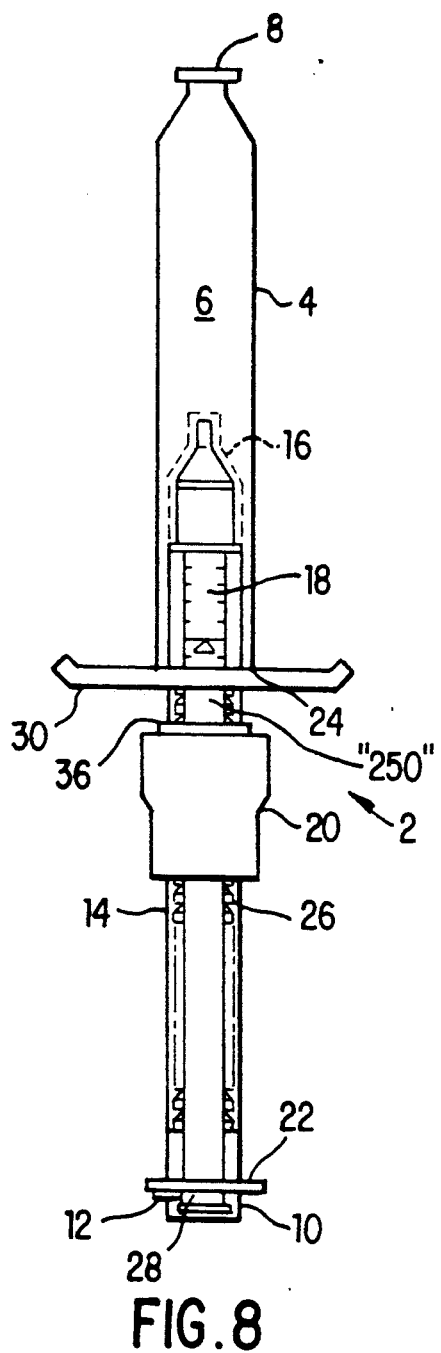

FIG. 8 of the drawings illustrates the same relative position between the plunger 14 and the container 4 as shown in FIG. 7, but the slide element 20 has been unlocked from its position on the plunger and retracted rearwardly relative to the plunger so that the "250" indicia on the scale 18 is now aligned with the rear wall 24 of the container. (As the slide element moves relative to the plunger, the scale 18 is rotated about its longitudinal support element 34 fixedly mounted relative to the plunger). This setting establishes that the next dosage of material 6 to be discharged from the container 4 will be of a quantity of "250". (This quantity has been arbitrarily selected for illustrative purposes, and it is clear that the user of the syringe may set any other quantity between zero and the full contents of the material remaining within the container, as desired.) Once the selected setting is indicated on the scale 18 by rearward movement of the slide element relative to the plunger, as discussed above, the slide element is releasably locked into its selected position in the manner previously described.

Figure 9:
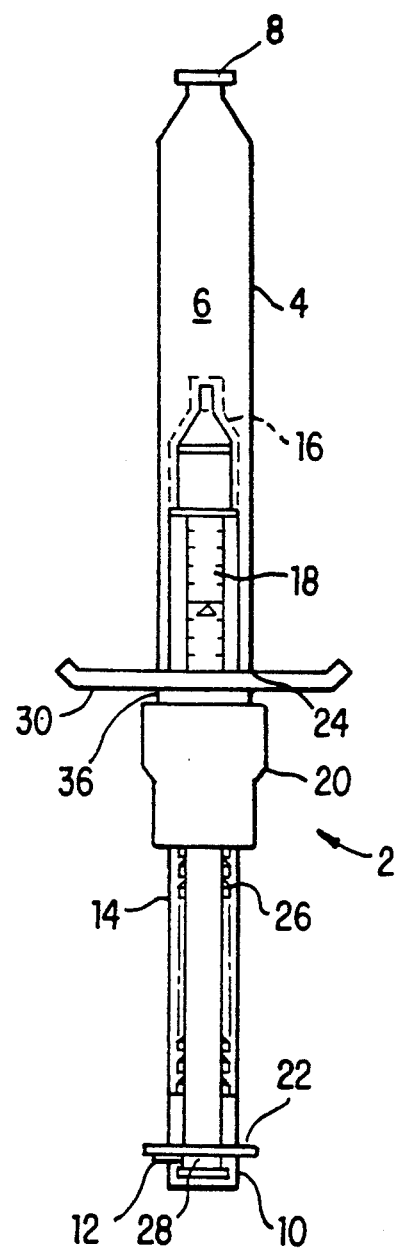

FIG. 9 illustrates the relative position of the plunger 14 and the container 4 after the plunger has been advanced forwardly from the position illustrated in FIG. 8 to its maximum forwardmost position relative to the container 4. As the plunger is advanced forwardly relative to the container, it is further received within the container, and forces discharge of the material 6 within the container through the forward discharge outlet 8 thereof, until such further forward relative movement is again stopped by the engagement of the front edge of the slide and the rear wall of the container. When this occurs, the quantity of material which has been discharged from the container corresponds to the quantity of material (e.g., "250") that had been set on the scale 18 prior to commencement of the further forward movement of the plunger relative to the container as a result of the calibration of the scale which corresponds to the quantity of material within the container. When the slide element is advanced to its forwardmost position relative to the rear wall of the container as a result of the forward movement of the plunger relative to the container as illustrated in FIG. 9, the zero indicia on the scale 18 again will be in alignment with the rear wall 24 of the container because the scale has advanced conjointly with the locked slide element and the plunger.

FIGS. 6–9 illustrate the "zero reset" feature of the syringe in accordance with the present invention. As described, the initial dose of "500" was selected by movement of the slide element rearwardly relative to the plunger, and was administered by forward movement of the plunger relative to the container until such forward movement was stopped by the slide element. When the pre-set dosage has been discharged, the zero indicia on the scale is in alignment with the rear wall 24 of the container. The next dosage to be administered, which can be the same or different from the prior dosage, is set by retracting the slide element and the scale relative to the plunger until the scale indicia corresponding to the absolute value of the desired quantity is aligned with the rear wall 24 of the container. The slide element is locked into position on the plunger, and the administration procedure is repeated. It is apparent that subsequent doses to be administered are each preset based only on the absolute value of the quantity to be discharged in the next successive dose, without reference to, or calculations involving, the quantity of material previously discharged from the syringe, or the quantity of material still remaining in the syringe. The elimination of such calculations and adjustments in computing the setting for the next dosage to be administered significantly reduces potential setting errors and enables more rapid and efficient use of the syringe to administer a sequence of successive, separate, multiple dosages, each of which may be of the same or different in quantity than prior dosages.

The user of the syringe may readily determine the quantity of material 6 remaining in the forward container 4 at any time during the administration sequence described above. As discussed, the indicia on the scale 18 ranges between zero contents and the maximum capacity of the container 4. By retracting the slide element 20, together with the scale 18, to its rearmost position on the plunger 14 (e.g., the rear plunger wall 22), the scale indicia aligned with the rear wall 24 of the container 4 will designate the actual quantity of material 6 still remaining within the container 4 at any relative position of the plunger and the container. The user may then set the next dosage to be administered at any quantity equal to or less than that remaining in the container. It is also apparent that the user may not set a subsequent dosage to exceed the remaining capacity of material 6 in a container 4 since the slide element 20 cannot be retracted relative to the plunger into any position in which indicia on the scale exceeding the contents remaining in the container will be aligned with the container rear wall. Therefore, the inability to move the slide to a position on the plunger which will set a selected quantity on the scale informs the user that the quantity of material remaining in the container is less than the desired dosage, and the indicia on the scale aligned with the rear container wall further informs the user of the specific quantity of contents remaining in the container.

In the preferred embodiment of the invention, the scale 18 is an endless, rotatable loop of tape mounted for rotation about a longitudinally extending support member fixedly mounted relative to, or within, the plunger. The tape loop can be formed from any suitable material, as for example, a flexible plastic or metal. As illustrated in FIG. 4, the rear wall 22 of the plunger is hingedly mounted at 32 between an opened and closed position to provide access within the plunger assembly to install, remove or repair the scale 18. However, the movable scale may be provided by embodiments other than a rotatable loop, as for example, a tape wound on a coil spring and having one end fixedly mounted proximate to the rear wall 24 of the container, and in which the tape is retractable rearwardly relative to the plunger by rearward movement of the slide element 20 against the opposing resilient force of the coil spring. As the retracted tape is moved forwardly either by movement of the slide element relative to the plunger, or by conjoint movement with the slide element and the plunger relative to the container, the tape will recoil around the coil spring. Other known or conventional means for providing a retractable measuring tape may also be employed in connection with the present invention.

Syringes in accordance with the present invention can be originally manufactured to include the zero reset feature described herein. It is also within the scope of the present invention to retrofit existing syringes to include the automatic zero reset feature.

FIGS. 1 and 4 of the drawings also illustrate other advantageous features of a syringe in accordance with the present invention. The forward end 16 of the plunger 14 is configured to complement the tapered configuration of the forward end of the container 4. Accordingly, the plunger end 16 will be fittingly received within the forward end of the container when the plunger is advanced into its forwardmost position relative to the container. The complementary structure of the respective forward ends of the plunger and container assures that substantially all material 6 will be discharged from the container 4 leaving only minimal residue therein. The tapered configuration of the complementary fit enables the container discharge outlet or nozzle 8 to define a relatively narrow opening which is essential to proper control and discharge of the material 6 from the syringe.

The protuberance 28 projecting outwardly from the rear wall 22 of the plunger provides means for removably receiving and storing the discharge outlet cap 10 when the cap is removed from the discharge outlet 8 at the front of the container during operation of the syringe. (See FIGS. 6-9). Preferably, the cap 10 is received on the projection 28 in a friction fit relationship, and the cap may be readily removed from both the discharge outlet and the projection 28 by means of the tab 12 extending from the cap. Loss of the cap during operation of the syringe is prevented by providing storage means for the cap integrally formed on the syringe itself.

FIG. 1 of the drawing also illustrates a wide handle 30 extending radially outwardly from the rear wall 24 of the container 4. The wide handle enables a user to operate the syringe with one hand, freeing the other hand to control the subject (which may be an animal receiving medication) during the administration procedure.

The syringes of the present invention are particularly useful in the application of veterinary medicines, but may also be employed for any application performed by known and conventional syringes. The syringes may be of either the preloaded, disposable type, or of the refillable, reusable type.

Other modifications within the scope of the present invention will become apparent to those skilled in the art. The description herein of the preferred embodiments is intended to be illustrative only, and not restrictive of the scope of the invention, that scope being defined by the following claims and all equivalents thereto.

I claim:

1. In a syringe including a container for storing material to be discharged therefrom, a plunger mounted behind said container and having a forward end adapted to be received within a rear opening in said container for selective movement thereof relative to said container for discharging material from said container, and means for measuring the quantity of material to be discharged from said container, the improvement comprising:

said means for measuring including a scale calibrated to correspond to the quantity of material within said container, means for selectively moving said scale relative to said container conjointly with said plunger, and means for selectively moving said scale relative to said plunger, said scale comprising an endless loop mounted for selective rotation about a supporting element fixedly mounted relative to said plunger.

2. The improvement as claimed in claim 1 wherein said means for selectively moving said scale relative to said plunger includes a slide element mounted to said plunger and selectively slideable therealong, and means for mounting said scale to said slide element for providing said selective movement of said scale relative to said plunger conjointly with said selective movement of said slide element relative to said plunger.

3. The improvement as claimed in claim 2 wherein said scale includes a zero indicia corresponding to zero contents of material within said container, said scale being mounted to said slide element such that said zero indicia is aligned with said slide element, said scale being movable relative to said plunger by said slide element to display other indicia on said scale corresponding to different preselected quantities of said material to be discharged from said container at a fixed position on said syringe.

4. The improvement as claimed in claim 3 wherein said scale is oriented relative to said plunger such that retraction of said slide element away from said container to a predetermined position on said plunger causes indicia on said scale corresponding to the quantity of said material remaining in said container to move into alignment with said fixed position on said syringe.

5. The improvement as claimed in claim 4 wherein said predetermined position on said plunger is a rear end wall of said plunger.

6. The improvement as claimed in claim 3 wherein said slide element is a stop for preventing relative movement of said plunger towards said container after a preselected quantity of said material has been discharged from said container.

7. The improvement as claimed in claim 3 wherein said scale is calibrated and oriented relative to said plunger such that said zero indicia on said scale is moved proximate to a forwardmost portion of the plunger extending rearwardly from said container after a preselected quantity of material has been discharged from said container.

8. The improvement as claimed in claim 2 wherein said slide element includes a locking element for selectively and releasably engaging locking means on said plunger, said slide element being pivotal between a first position in which said locking element is engaged with said locking means on said plunger and said slide element is locked in position relative to said plunger, and a second position in which said locking element is disengaged from said locking means on said plunger to permit selective movement of said slide element relative to said plunger.

9. The improvement as claimed in claim 1 further including a removable cap for covering a discharge opening defined in said container, said syringe including means for removably storing said cap when said cap is removed from said discharge opening.

10. The improvement as claimed in claim 9 wherein said plunger includes a rear wall and said means for removably storing said cap is defined as a projection extending from said rear wall.

11. The improvement as claimed in claim 1 wherein said plunger defines a rear opening therein and a rear wall is pivotally mounted over said rear opening for movement between a first position in which said rear opening is closed by said rear wall and a second position in which said rear opening is opened to provide access to said calibrated scale carried by said plunger.

12. The improvement as claimed in claim 1 wherein a front portion of said container is inwardly tapered and defines a discharge outlet at the forward end thereof, and a front portion of said plunger is inwardly tapered and complementary received within said front portion of said container when said plunger is moved to its forwardmost position relative to said container.

13. The improvement as claimed in claim 1 wherein said container includes a handle fixedly mounted proximate to the rear end thereof.

14. A syringe comprising a container for holding material to be discharged therefrom, a plunger received in a rear opening of said container and movable forwardly relative to said container for selectively discharging said material from said syringe, a scale carried by said plunger, said scale having indicia thereon corresponding to the quantity of said material in said container, and means for selectively moving said scale relative to said plunger for pre-setting a desired quantity of material to be discharged from said container when said plunger is advanced a predetermined distance into said container, said scale being oriented relative to said plunger such that it is re-set to a predetermined reference value after said plunger is advanced said predetermined distance into said container, said scale comprising an endless loop mounted for selective rotation about a supporting element fixedly mounted relative to said plunger.

15. The syringe as claimed in claim 14 wherein said predetermined reference value is a zero indicia on said scale.

* * * * *